United States Patent
Song et al.

(10) Patent No.: US 8,916,732 B2
(45) Date of Patent: Dec. 23, 2014

(54) METHOD FOR PREPARING CHLOROHYDRINS AND METHOD FOR PREPARING EPICHLOROHYDRIN USING CHLOROHYDRINS PREPARED THEREBY

(75) Inventors: Won Seob Song, Ulsan (KR); Sung Yul Woo, Ulsan (KR); Boo Weon Song, Ulsan (KR); Seong Han Park, Ulsan (KR); Myoung Suk Kwon, Ulsan (KR)

(73) Assignee: Samsung Fine Chemicals Co., Ltd. (KR)

( * ) Notice: Subject to any disclaimer, the term of this patent is extended or adjusted under 35 U.S.C. 154(b) by 0 days.

(21) Appl. No.: 13/805,778

(22) PCT Filed: Jun. 8, 2011

(86) PCT No.: PCT/KR2011/004170
§ 371 (c)(1),
(2), (4) Date: Dec. 20, 2012

(87) PCT Pub. No.: WO2012/002649
PCT Pub. Date: Jan. 5, 2012

(65) Prior Publication Data
US 2013/0102798 A1 Apr. 25, 2013

(30) Foreign Application Priority Data
Jun. 30, 2010 (KR) .......... 10-2010-0063158

(51) Int. Cl.
| | |
|---|---|
| *C07C 31/34* | (2006.01) |
| *C07D 301/02* | (2006.01) |
| *C07C 29/62* | (2006.01) |
| *C07C 29/80* | (2006.01) |
| *C07D 303/08* | (2006.01) |
| *C07D 301/26* | (2006.01) |

(52) U.S. Cl.
CPC ............. *C07C 29/62* (2013.01); *C07C 29/80* (2013.01); *C07D 303/08* (2013.01); *C07D 301/26* (2013.01)
USPC .......................................... 568/844; 549/518

(58) Field of Classification Search
CPC ........ C07C 29/62; C07C 29/80; C07C 31/36; C07C 303/08; C07C 301/26
USPC ................... 549/518, 514; 568/844
See application file for complete search history.

(56) References Cited

FOREIGN PATENT DOCUMENTS

| CN | 101031532 A | 9/2007 |
|---|---|---|
| CN | 101208323 A | 6/2008 |

(Continued)

OTHER PUBLICATIONS

International Search Report with English Translation for International Application No. PCT/KR2011/004170 dated Feb. 16, 2012.

(Continued)

*Primary Examiner* — T. Victor Oh
(74) *Attorney, Agent, or Firm* — Cantor Colburn LLP

(57) ABSTRACT

A method of preparing chlorohydrins and a method of preparing epichlorohydrin using chlorohydrins prepared by using the same method are provided. The method is to prepare chlorohydrins by reacting polyhydroxy aliphatic hydrocarbon with a chlorination agent in the presence of a catalyst, and the method includes at least one combination of a series of unit operations including the following steps in the following stated order: a first reaction step; a water removal step; and a second reaction step, wherein the water removing step is performed by distillation operation based on a boiling point difference between constituents of a reaction mixture. The method of preparing epichlorohydrin includes reacting chlorohydrins prepared by using the method of preparing chlorohydrins with an alkaline agent.

33 Claims, 1 Drawing Sheet

(56) References Cited

FOREIGN PATENT DOCUMENTS

| | | |
|---|---|---|
| CN | 101541418 A | 9/2009 |
| CN | 101636370 A | 1/2010 |
| KR | 1020070034599 A | 3/2007 |
| KR | 1020080037613 A | 4/2008 |
| KR | 1020090032429 A | 4/2009 |
| WO | WO2006/100320 * | 9/2006 |
| WO | WO2009/041766 * | 4/2009 |
| WO | 2009066327 A1 | 5/2009 |

OTHER PUBLICATIONS

Written Opinion with English Translation for International Application No. PCT/KR2011/004170 dated Feb. 16, 2012.

Chinese Office Action with English Translation for Application No. 20118032066.3 dated Apr. 30, 2014.

* cited by examiner

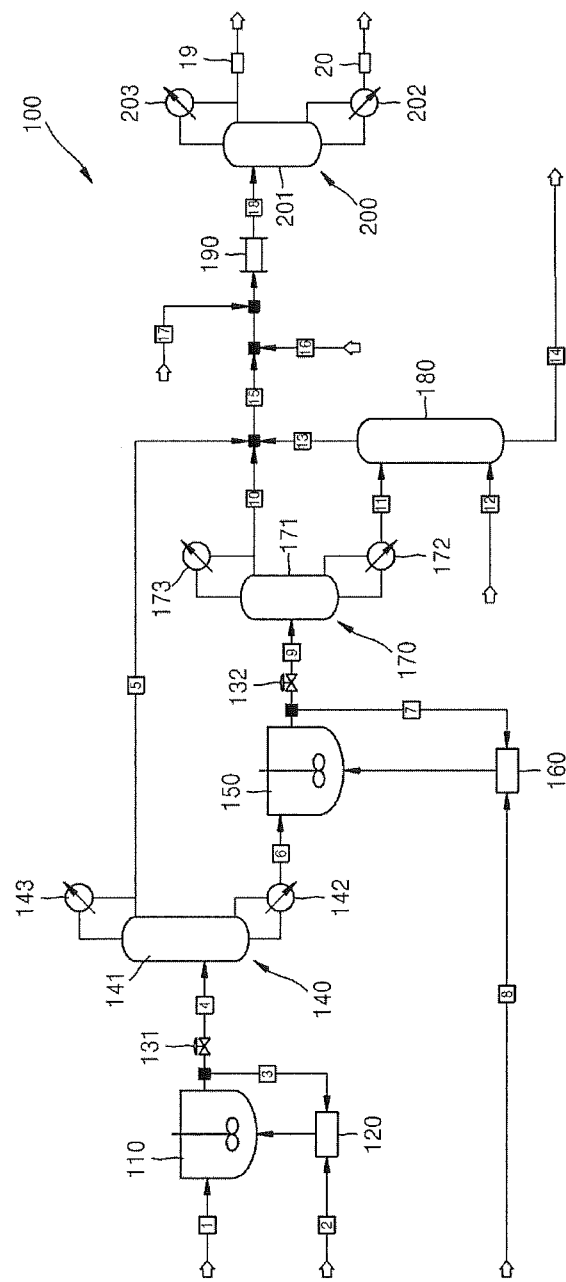

US 8,916,732 B2

METHOD FOR PREPARING CHLOROHYDRINS AND METHOD FOR PREPARING EPICHLOROHYDRIN USING CHLOROHYDRINS PREPARED THEREBY

TECHNICAL FIELD

The present invention relates to a method of preparing chlorohydrins and a method of preparing epichlorohydrin by using chlorohydrins prepared by using the method. In particular, the present invention relates to a method of preparing chlorohydrins by reacting polyhydroxy aliphatic hydrocarbon with a chlorination agent in the presence of a catalyst, the method including a plurality of reaction steps and a water removal step performed between the reaction steps, wherein the water removal step is performed for a reaction mixture having a particular composition ratio by distillation operation using a boiling point difference between constituents of the reaction mixture, and a method of preparing epichlorohydrin by reacting chlorohydrins prepared by using the method with an alkaline agent.

BACKGROUND ART

Currently, bio-diesel is competitively developed worldwide and produced, and even in Korea, the production of bio-diesel has been already begun and bio-diesel is commercially available as an additive of diesel oil.

In the procedure of producing bio-diesel, a great quantity of glycerol corresponding to about 10% of the production amount of the bio-diesel is produced. However, glycerol is excessively supplied in view of the demand thereof, and thus, the value of glycerol continuously decreases. Accordingly, there is a need to increase added-value of glycerol by converting glycerol into chlorohydrins, such as dichloropropanol.

Meanwhile, chlorohydrins, such as dichloropropanol, are used as a raw material for preparing epichlorohydrin, and the most of commercially available chlorohydrins are prepared from propylene. In particular, a method of preparing chlorohydrins includes preparing allyl chloride by high-temperature chlorination reaction of propylene and reacting the allyl chloride with a chlorination agent by using excess industrial water to prepare chlorohydrins. However, the method of preparing chlorohydrins using propylene has many problems including an unstable supply of propylene due to its price increase, generation of great quantities of waste water and waste matter, and excessive initial investment costs due to the two-step method and resulting difficulty in newly constructing/modifying of manufacturing apparatuses.

Accordingly, a one-step method of directly preparing chlorohydrins including reacting polyhydroxy aliphatic hydrocarbon, such as glycerol, which is a by-product of bio-diesel, with a chlorination agent in the presence of a catalyst is economical. The one-step method of preparing chlorohydrins by using polyhydroxy aliphatic hydrocarbon, such as glycerol, as reaction raw materials may have lower manufacturing costs due to the use of cheap polyhydroxy aliphatic hydrocarbon. In addition, during the preparation process, industrial water is not used, and thus, generation of waste water and waste matter may be predominantly reduced, thereby being environmentally friendly. Furthermore, the one-step method may contribute to a decrease in process and environment-related investment costs, leading to a lower initial investment costs.

However, the method of preparing chlorohydrins produces water as a by-product and the generated water inhibits a chlorination reaction of polyhydroxy aliphatic hydrocarbon, such as glycerol, so that as the reaction progresses, the reaction rate gradually decreases, the reaction time increases, and selectivity of chlorohydrins decreases.

DETAILED DESCRIPTION OF THE INVENTION

Technical Problem

An embodiment of the present invention provides a method of preparing chlorohydrins by reacting polyhydroxy aliphatic hydrocarbon with a chlorination agent in the presence of a catalyst, wherein the method includes a plurality of reaction steps and a water removal step performed between the reaction steps, wherein the water removal step is performed for a reaction mixture having a particular composition ratio by distillation operation using a boiling point difference between constituents of the reaction mixture.

Another embodiment of the present invention provides a method of preparing epichlorohydrin, wherein the method includes reacting chlorohydrins prepared by using the method of preparing chlorohydrins, with an alkaline agent.

Technical Solution

According to an aspect of the present invention, there is provided a method of preparing chlorohydrins by reacting polyhydroxy aliphatic hydrocarbon with a chlorination agent in the presence of a catalyst, the method comprising at least one combination of a series of unit operations comprising the following steps in the following stated order: a first reaction step for reacting polyhydroxy aliphatic hydrocarbon with a chlorination agent; a water removal step for removing water as a by-product from a reaction mixture discharged from the first reaction step; and a second reaction step for reacting at least one constituent of the reaction mixture from which water is removed, with at least one of the chlorination agent and an additional chlorination agent, wherein the reaction mixture introduced into the water removal step includes polyhydroxy aliphatic hydrocarbon, chlorohydrins, and an intermediate product as a reaction product of the catalyst and the polyhydroxy aliphatic hydrocarbon at a ratio of 0 to 90 parts by weight of the polyhydroxy aliphatic hydrocarbon: 5 to 95 parts by weight of the chlorohydrins: 5 to 12 parts by weight of the intermediate product, and the water removal step is performed by distillation based on a boiling point difference between constituents of the reaction mixture added to the water removal step.

According to an aspect of the present invention, there is provided A method of preparing chlorohydrins, the method comprising: introducing polyhydroxy aliphatic hydrocarbon, a catalyst, and a chlorination agent into a first reactor in which the temperature is maintained in a range of 50 to 200° C.; discharging an effluent of the first reactor comprising water as a by-product from the first reactor; introducing at least a portion of the effluent of the first reactor effluent into a water removal device; and introducing the effluent of the first reactor from which water is removed, and an additional chlorination agent into a second reactor in which the temperature is maintained in a range of 80 to 200° C., wherein the effluent of the first reactor introduced into the water removal device comprises polyhydroxy aliphatic hydrocarbon, chlorohydrins, and an intermediate product as a reaction product of the catalyst and the polyhydroxy aliphatic hydrocarbon at a ratio of 0 to 90 parts by weight of the polyhydroxy aliphatic hydrocarbon: 5 to 95 parts by weight of the chlorohydrins: 5 to 12 parts by weight of the intermediate product, and the water removal device is operated by distillation operation based on a boiling point difference between constituents of the reaction mixture added to the water removal device.

The polyhydroxy aliphatic hydrocarbon may be a $C_2$ to $C_{20}$ compound that contains two or more hydroxyl groups bonded to different carbon atoms.

The polyhydroxy aliphatic hydrocarbon may include at least one compound selected from the group consisting of 1,2-ethanediol, 1,2-propanediol, 1,3-propanediol, 3-chloro-1,2-propanediol, 2-chloro-1,3-propanediol, glycerol, 1,2,4-butanetriol, 1,4-butanediol, and esters of these compounds.

The chlorohydrins may be a compound including at least one hydroxyl group and at least one chlorine atom that are bonded to different carbon atoms.

The chlorohydrins may include at least one compound selected from the group consisting of 3-chloro-1,2-propanediol, 2-chloro-1,3-propanediol, 1,3-dichloropropane-2-ol, and 2,3-dichloropropane-1-ol.

The catalyst may include at least one selected from the group consisting of an organic acid catalyst, a carboxylic acid-based catalyst, a nitrile-based catalyst, and a solid catalyst.

The intermediate product may act as a catalyst in a chlorination reaction of the polyhydroxy aliphatic hydrocarbon.

The polyhydroxy aliphatic hydrocarbon may include glycerol, the catalyst may include an acetic acid, and the intermediate product may include glycerol acetates.

The chlorination agent may include a hydrogen chloride gas or an aqueous hydrochloric acid solution.

The effluent of the first reactor introduced into the water removal device may be discharged when a conversion rate of the polyhydroxy aliphatic hydrocarbon is in a range of 30 to 100% and the yield of the chlorohydrins is in a range of 30 to 95%, in the first reactor.

The effluent of the first reactor introduced into the water removal device may include the chlorination agent and water at a ratio of 10 to 25.0 parts by weight of the total of the chlorination agent and the additional chlorination agent and 75 to 90 parts by weight of water.

A chlorination agent may be additionally introduced into the second reactor.

A retention time of the reactor contents in the first reactor may be in a range of 20 minutes to 1 hour, and a retention time of the reactor contents in the second reactor may be in a range of 1 to 3 hours.

The first reactor and the second reactor may be maintained at an atmospheric pressure or higher, and the water removal device may be maintained at an atmospheric pressure or lower.

The first reactor and the second reactor may be maintained at 1 to 20 atm, and the water removal device may be maintained at 10 to 760 mmHg.

The water removal device may include a vacuum distillation column having a theoretical plate number of 2 to 50.

The effluent of the first reactor may be decompressed in a decompression device and then introduced into the water removal device.

The decompression device may include a decompression valve.

The first reactor and the second reactor may be each independently a continuous stirred tank reactor, a batch reactor, a semi-batch reactor, or a plug flow reactor.

The effluent of the first reactor introduced into the water removal device may be divided into a water-rich layer and a water-deficient layer.

The method may further include: purifying chlorohydrins from an effluent of the second reactor to obtain chlorohydrins concentrate, and mixing the water-rich layer with the chlorohydrins concentrate to obtain a first composition of chlorohydrins.

The effluent of the second reactor may include 0 to 10 parts by weight of the polyhydroxy aliphatic hydrocarbon, 80 to 98 parts by weight of the chlorohydrins, 0 to 10 parts by weight of the total of the chlorination agent and the additional chlorination agent and 1 to 20 parts by weight of water.

The first composition of chlorohydrins may include 0 to 10 parts by weight of the polyhydroxy aliphatic hydrocarbon, 60 to 96 parts by weight of the chlorohydrins, 0 to 20 parts by weight of the total of the chlorination agent and the additional chlorination agent, and 0 to 30 parts by weight of water.

The method may further include diluting the first composition of chlorohydrins with water to obtain the second composition of chlorohydrins.

The water may be added in an amount of 100 to 500 parts by weight based on 100 parts by weight of the first composition of chlorohydrins.

According to some embodiments, a method of preparing epichlorohydrin, the method may include: contacting the second composition of chlorohydrins prepared according to claim 26 with an alkaline agent at a temperature of 20 to 100° C., and the second composition of chlorohydrins includes 0 to 5 parts by weight of the polyhydroxy aliphatic hydrocarbon, 10 to 40 parts by weight of the chlorohydrins, 0 to 5 parts by weight of the total of the chlorination agent and the additional chlorination agent and 50 to 90 parts by weight of water.

The second composition of chlorohydrins additionally may include a catalyst, and the catalyst reacts with the alkaline agent to form an alkali metal salt.

Advantageous Effects

According to an embodiment of the present invention, a method of preparing chlorohydrins provides an improved selectivity of chlorohydrins According to another embodiment of the present invention, a method of preparing epichlorohydrin includes reacting chlorohydrins prepared using the method with an alkaline agent.

DESCRIPTION OF THE DRAWINGS

FIG. 1 is a diagram illustrating a method of preparing chlorohydrins according to an embodiment of the present invention and a method of preparing epichlorohydrin using the prepared chlorohydrins according to an embodiment of the present invention.

BEST MODE

Hereinafter, a method of preparing chlorohydrins and a method of preparing epichlorohydrin, according to embodiments of the present invention, are described in detail. In the present specification, 'a method of preparing chlorohydrins' may also refer to a method of preparing a composition of chlorohydrins, in some cases.

The method of preparing a chlorohydrin according to the present embodiment includes reacting a polyhydroxy aliphatic hydrocarbon with a chlorination agent in the presence of a catalyst.

The chlorohydrins preparation method includes at least one combination of a series of unit operations including a plurality of reaction steps and a water removal step in the following stated order: a first reaction step for reacting polyhydroxy aliphatic hydrocarbon with a chlorination agent; a water removal step for removing water as a by-product from a reaction mixture discharged from the first reaction step; and a second reaction step for reacting at least one constituent of the reaction mixture from which water is removed with at least one of the chlorination agent and an additional chlorination agent. In addition, in the water removal step, a chlorination agent is not additionally added.

The reaction mixture introduced into the water removal step may include polyhydroxy aliphatic hydrocarbon, chlorohydrins, and an intermediate product as a reaction product of the catalyst and the polyhydroxy aliphatic hydrocarbon at a ratio of 0 to 90 parts by weight of the polyhydroxy aliphatic hydrocarbon: 5 to 95 parts by weight of the chlorohydrins: 5 to 12 parts by weight of the intermediate product, and the water removal step is performed by distillation process based on a boiling point difference of constituents of the reaction mixture added to this process.

Hereinafter, the method of preparing chlorohydrins will be described in detail with reference to FIG. 1.

In this specification, 'chlorohydrins' refers to chlorohydrins, esters of chlorohydrins, or a mixture thereof.

The chlorohydrins may be a compound having at least one hydroxyl group and at least one chlorine atom which are bonded to different carbon atoms. For example, the chlorohydrins may include at least one compound selected from the group consisting of 3-chloro-1,2-propanediol, 2-chloro-1,3-propanediol, 1,3-dichloropropane-2-ol, and 2,3-dichloropropane-1-ol. In the present specification, 3-chloro-1,2-propanediol and 2-chloro-1,3-propanediol are collectively referred to as "monochloropropanediol," and 1,3-dichloropropane-2-ol and 2,3-dichloropropane-1-ol are collectively referred to as "dichloropropaneol."

In the method of preparing a chlorohydrins according to an embodiment of the present invention, 1,3-dichloropropane-2-ol is predominantly produced, and particularly, suitable for use as a reaction raw material to prepare epichlorohydrin.

Referring to FIG. 1, polyhydroxy aliphatic hydrocarbon and a catalyst are introduced into a first reactor 110 via a line 1. In addition, a chlorination agent is introduced into the first reactor 110 via a line 2 and/or other paths.

The polyhydroxy aliphatic hydrocarbon may be a $C_2$-$C_{20}$ compound having at least two hydroxyl groups bonded to different carbon atoms. The polyhydroxy aliphatic hydrocarbon may include at least one compound selected from the group consisting of 1,2-ethanediol, 1,2-propanediol, 1,3-propanediol, 3-chloro-1,2-propanediol, 2-chloro-1,3-propanediol, glycerol, 1,2,4-butanetriol, 1,4-butanediol, and esters of these compounds.

The catalyst may be an organic acid catalyst, a carboxylic acid-based catalyst, a nitrile-based catalyst, a solid catalyst, or a mixture of at least two of these catalysts.

The organic acid catalyst may include, for example, at least one compound selected from the group consisting of a monocarboxylic acid, a dicarboxylic acid, a polycarboxylic acid, a malonic acid, a levulinic acid, a citric acid, a succinic acid, a propionic acid, and derivatives of these organic acids.

The carboxylic acid-based catalyst may include, for example, at least one compound selected from the group consisting of monocarboxylic acid ester, polycarboxylic acid ester, monocarboxylic acid anhydrides, polycarboxylic acid anhydrides, monocarboxylic acid chlorides, polycarboxylic acid chlorides, monocarboxylic acid salts, polycarboxylic acid salts, and derivatives of these carboxylic acid based compounds.

The nitrile-based catalyst may include, for example, at least one compound selected from the group consisting of acetonitrile, propionitrile, acrylonitrile, valeronitrile, isobutyronitrile, hydroxyacetonitrile, chloroacetonitrile, succinonitrile, glutaronitrile, adiponitrile, and phenylacetonitrile.

The solid catalyst may include, for example, at least one compound selected from the group consisting of an inorganic oxide, an inorganic halide, a strong-acidic organic compound, and mixtures of at least two of these.

The inorganic oxide may include at least one compound selected from the group consisting of metal oxide, composite oxide, oxy acid, and oxy acid salt. The metal oxide may be, for example, $SiO_2$, $Al_2O_3$, $TiO_2$, $Fe_2O_3$, $ZrO_2$, $SnO_2$, $CeO_2$, $Ga_2O_3$, or $La_2O_3$. The composite oxide may be, for example, $SiO_2$—$Al_2O_3$, $SiO_2$—$TiO_2$, $TiO_2$—$ZrO_2$, $SiO_2$—$ZrO_2$, $MoO_3$—$ZrO_2$, zeolite, a heteropoly acid (i.e., a poly acid including P, Mo, V, W, Si or the like), or a heteropoly acid salt. Examples of the oxy acid and oxy acid salt include $BPO_4$, $AlPO_4$, poly phosphoric acid, acidic phosphate, $H_3BO_3$, acidic borate, and niobic acid.

The inorganic halide may be a metal halide such as a metal fluoride, a metal chloride, a metal bromide, or a metal iodide of a Group 3A element such as scandium, yttrium, lanthanum, or actinium; a Group 4A element such as titanium, zirconium, or hafnium; a Group 5A element such as vanadium, niobium, or tantalum; a Group 8 element such as iron, cobalt, nickel, palladium, or platinum; a Group 2B element such as zinc; a Group 3B element such as aluminum or gallium; or a Group 4B element such as germanium or tin.

The strong acidic organic compound may be, for example, an organic sulfonic acid compound such as a sulfonate group-containing ion-exchange resin or a condensed carbon ring-containing sulfonic acid compound.

The amount of the catalyst introduced may be from 1 to 10 parts by weight based on 100 parts by weight of the polyhydroxy aliphatic hydrocarbon. When the amount of the catalyst introduced is within this range, a reaction rate may be satisfactorily improved with an appropriate amount of the catalyst.

In the method of preparing the chlorohydrin, the first reactor 110 may be maintained at a temperature from 50 to 200° C. When the temperature of the first reactor 110 is within this range, a high reaction rate may be obtained by the application of an appropriate level of energy. In addition, the first reactor 110 may be maintained at an atmospheric pressure or higher, for example, at 1 to 20 atm. When the pressure of the first reactor 110 is within this range, relatively high reaction activity may be obtained. In this case, even when the pressure of the first reactor 110 is greater than 20 atm, an effect of an increase in reaction activity according to the increase in pressure is not significant. In addition, the first reactor 110 may be a continuous stirred tank reactor (CSTR), but is not limited thereto. For example, the first reactor 110 may be a batch reactor, a semi-batch reactor, or a plug flow reactor. In the first reactor 110, in addition to chlorohydrins as a main product, a reaction product of the catalyst and the polyhydroxy aliphatic hydrocarbon as an intermediate product is produced. The intermediate product may act as a catalyst in the chlorination of the polyhydroxy aliphatic hydrocarbon (e.g., a reaction for producing chlorohydrins which occurs in the first reactor 110 and/or a second reactor 150.) For example, when the polyhydroxy aliphatic hydrocarbon includes glycerol and the catalyst includes acetic acid, the intermediate product may include glycerol acetates. As used herein, the term "glycerol acetates" indicates a substituted or unsubstituted glycerol monoacetate, a substituted or unsubstituted glycerol diacetate, a substituted or unsubstituted glycerol triacetate, or a mixture of these compounds. In addition, the term "substituted" as used herein means that a hydrogen atom of a compound is substituted with a halogen group, a hydroxyl group, an alkyl group, an alkoxy group, an amine group, or a combination thereof. In addition, a retention time of the reactor contents in the first reactor 110 may be from 20 minutes to 1 hour. When the retention time of the reactor contents in the first reactor 110 is within this range, a high conversion rate of the polyhydroxy aliphatic hydrocarbon may be obtained within an appropriate period of time.

The chlorination agent may include a hydrogen chloride gas or an aqueous hydrochloric acid solution.

An example of the reaction occurring in the first reactor 110 is the chlorination reaction of polyhydroxy aliphatic hydrocarbon (e.g., glycerol) which is represented by Reaction Scheme 1 below:

The first mixing device 120 may include an ejector, an inline mixer, an ultrasonic mixture, or a mixture of at least two of these. When an ejector is used as the first mixing device 120, the first reactor effluent may act as a motive fluid and the chlorination agent may act as a suction fluid.

The decompression device 131 may include a decompression valve.

The additional chlorination agent may include a hydrogen chloride gas or an aqueous hydrochloric acid solution.

The water removal device 140 may be operated by distillation operation based on a boiling point difference between constituents of the first reactor effluent.

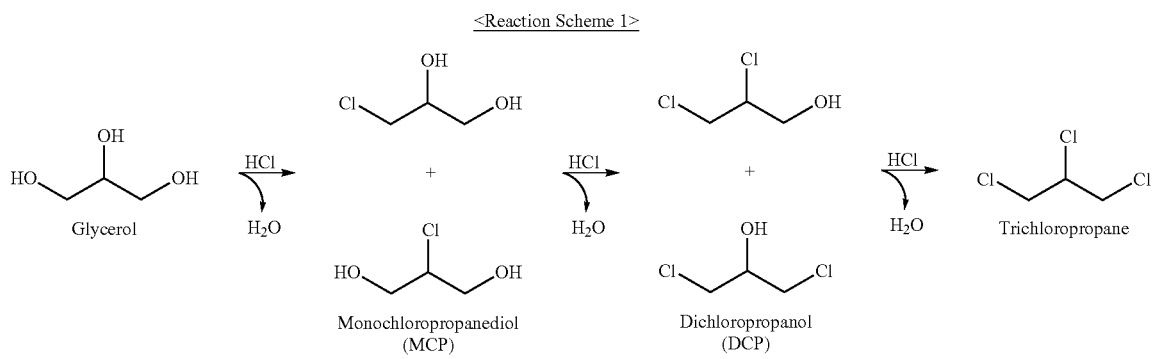

<Reaction Scheme 1>

In the above reaction, the conversion rate of glycerol, the yield of monochloropropanediol (MCP), the yield of dichloropropanol (DCP), the selectivity of monochloropropanediol (MCP), and the selectivity of DCP may be calculated respectively by Equations 1 through 5 below:

Conversion rate of glycerol(%)=(number of moles of glycerol reacted)/(number of moles of glycerol introduced)×100; [Equation 1]

Yield of MCP(%)=(number of moles of monochloropropanediol generated)/(number of moles of glycerol introduced)×100; [Equation 2]

Yield of DCP(%)=(number of moles of DCP generated)/(number of moles of glycerol introduced)×100; [Equation 3]

Selectivity of monochloropropanediol(MCP)=(number of moles of MCP generated)/(total number of moles of reaction products)×100;and [Equation 4]

Selectivity of dichloropropanol(DCP)=(number of moles of DCP generated)/(total number of moles of reaction products)×100. [Equation 5]

After the retention time elapses, a first reactor effluent is discharged from the first reactor 110 and flows into a line 3 and/or a line 4. That is, at least a portion of the first reactor effluent flows into a first mixing device 120 via the line 3, and the remaining portion of the first reactor effluent is decompressed in a decompression device 131 and then flows into a water removal device 140 via the line 4. Herein, the first reactor effluent may include a catalyst; chlorohydrins; an intermediate product such as glycerol acetates; water; unreacted polyhydroxy aliphatic hydrocarbon; and/or a chlorination agent. In addition, the chlorination agent is introduced into the first mixing device 120 via the line 2. In the first mixing device 120, the first reactor effluent is mixed with the chlorination agent and then recycled to the first reactor 110.

In addition, the water removal device 140 may be maintained at an atmospheric pressure or lower, for example, at 10 to 760 mmHg. When the pressure of the water removal device 140 is within this range, a temperature of a downstream effluent (i.e., water-deficient layer) is appropriate, and thus, an amount of high boiling point material generated is decreased and clogging of the water removal device 140 and pipelines may be prevented. The water removal device 140 may include a vacuum distillation column having a theoretical plate number of 2 to 50 (i.e., a dehydration column 141). When the theoretical plate number of the vacuum distillation column is within this range, the amount of moisture remaining in the water-deficient layer may be minimized. As used herein, the term "theoretical plate number" indicates the number of imaginary regions or plates where two phases, such as gas and liquid phases, reach equilibrium, in a separation process using the vacuum distillation column.

The first reactor effluent introduced into the water removal device 140 may be discharged when the conversion rate of the polyhydroxy aliphatic hydrocarbon is in a range of 30 to 100% and the yield of the chlorohydrins is in a range of 30 to 95%, in the first reactor 110. In the first reactor effluent introduced into the water removal device 140, when the conversion rate of the polyhydroxy aliphatic hydrocarbon and the yield of the chlorohydrins are within the ranges described above, a decrease in a reaction rate in the first reactor 110 does not occur and the water removal device 140 may have high water removal effects. In addition, a high selectivity of chlorohydrins in the first reactor 110 may be obtained. For example, the first reactor effluent introduced into the water removal device 140 may include 0 to 90 parts by weight of the polyhydroxy aliphatic hydrocarbon, 5 to 95 parts by weight of the chlorohydrin, and 5 to 12 parts by weight of the intermediate product (e.g., glycerol acetates).

In addition, the first reactor effluent introduced into the water removal device 140 may include 10 to 25 parts by weight of the total of the chlorination agent and the additional chlorination agent and 75 to 90 parts by weight of water. When the amounts of the chlorination agent and the water are within the ranges described above, the first reactor effluent may form an azeotropic mixture, and thus, the solubility of the chlorination agent with respect to the water increases so that a loss of the chlorination agent may be minimized.

The first reactor effluent introduced into the water removal device 140 via the line 4 is separated into a gas phase material and other materials (i.e., a liquid phase material and a solid phase material) in a dehydration column 141. Thereafter, the gas phase material is condensed in a condenser 143 and flows into a line 5, and the other materials are distilled in a reboiler 142 and separated again into a gas phase material and other materials. Afterwards, the gas phase material is recycled to the dehydration column 141 and the other materials flow into the second reactor 150 via a line 6. In particular, a material (hereinafter, referred to as "water-rich layer") that is condensed in the condenser 143 and flows into the line 5 after being discharged from an upper portion of the dehydration column 141 may include water and a chlorination agent, and a material (hereinafter, referred to as "water-deficient layer") that does not vaporize in the reboiler 142 and flows into the line 6 after being discharged from a lower portion of the dehydration column 141 may include an unreacted polyhydroxy aliphatic hydrocarbon, chlorohydrins, and/or the above-described intermediate product. The intermediate product is introduced into the second reactor 150 and acts as a catalyst for the chlorination reaction of Reaction Scheme 1, and thus, the reaction may smoothly occur in the second reactor 150 without further adding a catalyst.

The reboiler 142 and the condenser 143 may be maintained at 100 to 200° C. and 0 to 60° C., respectively.

The second reactor 150 may be maintained at 70 to 200° C. When the temperature of the second reactor 150 is within the range described above, chlorohydrins may be obtained with a high yield by the application of an appropriate level of energy. In addition, the second reactor 150 may be maintained at an atmospheric pressure or higher, for example, 1 to 20 atm. When the pressure of the second reactor 150 is within this range, the solubility of the chlorination agent with respect to the contents of the second reactor 150 may be improved. The second reactor 150 may be a CSTR, but is not limited thereto. For example, the second reactor 150 may be a batch reactor, a semi-batch reactor, or a plug flow reactor. In the second reactor 150, chlorohydrins are additionally generated by contacting the above-described intermediate product with an additional chlorination agent that is separately added to the second reactor 150. The retention time of the reactor contents in the second reactor 150 may be from 1 to 3 hours. When the retention time of the second reactor contents is within this range, chlorohydrins may be obtained with a high yield within an appropriate period of time.

The reaction that occurs in the second reactor 150 is the same as or similar to that occurring in the first reactor 110.

After the retention time elapses, a second reactor effluent is discharged from the second reactor 150 and introduced into a line 7 and/or a line 9. That is, at least a portion of the second reactor effluent is introduced into a second mixing device 160 via the line 7, and the remaining portion of the second reactor effluent is decompressed in a second decompression device 132, and then, introduced into a first distillation device 170 via a line 9. In this regard, the second reactor effluent may include a catalyst; chlorohydrins; an intermediate product such as glycerol acetates; water; an unreacted polyhydroxy aliphatic hydrocarbon; and/or a chlorination agent. The additional chlorination agent is introduced into the second mixing device 160 via a line 8. In the second mixing device 160, the second reactor effluent is mixed with the additional chlorination agent, and the resulting mixture is then recycled to the second reactor 150. The additional chlorination agent may be introduced into the second reactor 150 via other paths, in addition to the line 8.

The second mixing device 160 may include an ejector, an inline mixer, an ultrasonic mixture, or a mixture of at least two of these. When an ejector is used as the second mixing device 160, the second reactor effluent may act as a motive fluid and the additional chlorination agent may act as a suction fluid.

The second decompression device 132 may include a decompression valve.

The first distillation device 170 may be operated by distillation operation based on a boiling point difference between constituents of the second reactor effluent.

In addition, the first distillation device 170 may be maintained at an atmospheric pressure or lower, for example, 10 to 760 mmHg. When the pressure of the first distillation device 170 is within the range described above, chlorohydrins may be separated with a high efficiency. The first distillation device 170 may include a vacuum distillation column having a theoretical plate number of 2 to 50 (i.e., a separation column 171). When the theoretical plate number of the vacuum distillation column is within this range, chlorohydrins may be separated with a high efficiency.

The second reactor effluent introduced into the first distillation device 170 may include 0 to 10 parts by weight of the polyhydroxy aliphatic hydrocarbon, 80 to 98 parts by weight of the chlorohydrins, 0 to 10 parts by weight of the total of the chlorination agent and the additional chlorination agent, and 1 to 20 parts by weight of water. When the amounts of the constituents of the second reactor effluent are within the range described above, the reaction is completed and thus the yield of the chlorohydrins is maximized.

The second reactor effluent that is introduced into the first distillation device 170 via the line 9 is separated into a gas phase material and a liquid phase material in the separation column 171. Thereafter, the gas phase material is condensed in a second condenser 173 and flows into a line 10, and the liquid phase material is distilled in a second reboiler 172 and separated again into a gas phase material and a liquid phase material. Afterwards, the gas phase material is recycled to the separation column 171 and the liquid phase material is introduced into a stripping device 180 via a line 11. In particular, a material that is condensed in the second condenser 173 and flows into the line 10 after being discharged from an upper portion of the separation column 171 may include chlorohydrins, water and/or a chlorination agent, and a high boiling point material that does not vaporize in the second reboiler 172 and flows into the line 11 after being discharged from a lower portion of the separation column 171 may include an intermediate product, such as glycerol acetates. In this regard, a considerable amount of chlorohydrins may flow into the line 11 together with the intermediate product. Herein, the second reboiler 172 and the second condenser 173 may be maintained at a temperature of 100 to 200° C. and 0 to 60° C., respectively.

In the first distillation device 170, a chlorination reaction of the polyhydroxy aliphatic hydrocarbon, i.e., a reaction for generating chlorohydrins, may further occur.

The stripping device 180 separates a low boiling point material such as chlorohydrins that is introduced together with the high boiling point material via the line 11 by using steam that is supplied via a line 12. The low boiling point material that is collected by the stripping device 180 flows into a line 13, and the high boiling point material is discharged to the outside via a line 14.

The first distillation device 170 and the stripping device 180 are collectively referred to as a chlorohydrins refiner.

The materials that are introduced into the lines 10 and 13 are collectively referred to as a concentrate of chlorohydrins.

The materials that are introduced into the lines 5, 10 and 13 may be combined together at a single location to form a first composition of chlorohydrins.

The first composition of chlorohydrins may include 0 to 10 parts by weight of the polyhydroxy aliphatic hydrocarbon, 60 to 96 parts by weight of the chlorohydrins, 0 to 20 parts by weight of the total of the chlorination agent and the additional chlorination agent, and 0 to 30 parts by weight of water.

When the method of preparing the chlorohydrins as described above is used, water, which is a by-product, is removed without loss of the chlorination agent and/or the catalyst, and thus, a reduction in reaction rate may be prevented and the selectivity of chlorohydrins may be increased.

The first composition of chlorohydrins may be used to prepare epichlorohydrin. In this regard, the first composition of chlorohydrins may be diluted with water before being used to prepare epichlorohydrin to form a second composition of chlorohydrins. In particular, referring to FIG. 1, the first composition of chlorohydrins introduced via a line 15 may be mixed with water introduced via a line 16 to form a second composition of chlorohydrins. This is because when epichlorohydrin is prepared using a high concentration of chlorohydrins, the amount of by-products produced increases and thus the selectivity of the epichlorohydrin is decreased. In the diluting process, the amount of the water added may be from 100 to 500 parts by weight based on 100 parts by weight of the first composition of chlorohydrins. When the amount of the water added is within this range, the amount of by-products may be reduced by an appropriate amount of water, and thus, the yield of the epichlorohydrin may be maximized.

The second composition of chlorohydrins may be used as a reactant for the preparation of epichlorohydrin along with an alkaline agent. The second composition of chlorohydrins may include 0 to 5 parts by weight of the polyhydroxy aliphatic hydrocarbon, 10 to 40 parts by weight of the chlorohydrins, 0 to 5 parts by weight of the total of the chlorination agent and the additional chlorination agent, and 50 to 90 parts by weight of water.

When the amounts of constituents of the second composition of chlorohydrins are within the ranges described above, the amounts of by-products decreases, and thus, the yield of the epichlorohydrin may be maximized.

In an inline reactor 190, the second composition of chlorohydrins may contact an alkaline agent (e.g., an aqueous sodium hydroxide solution) introduced via a line 17, which causes the following two reactions to occur. That is, while the second composition of chlorohydrins contacts the alkaline agent, the pH of a mixture of the second composition of chlorohydrins and the alkaline agent gradually increases as the contact time elapses. Herein, when the pH of the mixture thereof is 7 or below, the catalyst of the second composition of chlorohydrins may react with the alkaline agent to form an alkali metal salt. The formed alkali metal salt may be precipitated and then removed in a second distillation device 200, which will be described below. On the other hand, when the pH of the mixture thereof is greater than 7, the chlorohydrins (e.g., dichloropropanol) of the second composition of chlorohydrins may react with the alkaline agent to form epichlorohydrin. Herein, the inline reactor 190 may be maintained at a temperature of 20 to 100° C. and at a pressure of 1 to 2 atm. When the temperature and pressure of the inline reactor 190 are within this range, the reaction may smoothly progress by the application of an appropriate energy.

In addition, the first composition of chlorohydrins may include the above-described catalyst, and accordingly, the second composition of chlorohydrins may also include the catalyst. Consequently, the two reactions may occur in the inline reactor 190: a reaction for forming epichlorohydrin, which is a main product; a reaction for forming an alkali metal salt by contacting the catalyst with the alkaline agent.

As described above with reference to FIG. 1, the second composition of chlorohydrins is formed by adding water to the first composition of chlorohydrins (i.e., the composition introduced via the line 15) and the alkaline agent is added to the second composition of chlorohydrins; however, the present invention is not limited thereto. For example, the second composition of chlorohydrins may be prepared by directly adding an alkaline agent to the first composition of chlorohydrins to remove the catalyst and then adding water to the first composition of chlorohydrins from which the catalyst is removed. That is, in FIG. 1, the locations of the lines 16 and 17 may be switched to each other.

A material including the epichlorohydrin and the alkali metal salt which has been discharged from the inline reactor 190 is introduced into the second distillation device 200 via a line 18.

The second distillation device 200 may be operated by distillation operation based on a boiling point difference between constituents of the material including the epichlorohydrin and the alkali metal salt.

In addition, the second distillation device 200 may be maintained at an atmospheric pressure or lower, for example, 10 to 760 mmHg. When the pressure of the second distillation device 200 is within the range described above, epichlorohydrin may be separated with a high efficiency. The second distillation device 200 may include a vacuum distillation column having a theoretical plate number of 2 to 50 (i.e., a separation column 201). When the theoretical plate number of the vacuum distillation column is within this range, epichlorohydrin may be separated with a high efficiency.

The effluent of the inline reactor 190 introduced into the second distillation device 200 via the line 18 is separated into a gas phase material and a liquid phase material in the separation column 201. Thereafter, the gas phase material is condensed in a second condenser 203 and flows into a line 19 and then collected, and the liquid phase material is distilled in a second reboiler 202 and separated again into a gas phase material and a liquid phase material. Afterwards, the gas phase material is recycled to the separation column 201 and the liquid phase material is discharged to the outside via a line 20. In particular, a material that is condensed in the second condenser 203 and flows into the line 19 after being discharged from an upper portion of the separation column 201 may include epichlorohydrin and water, and a high boiling point material that is discharged to the outside via the line 20 without evaporation in the reboiler 202 after being discharged from a lower portion of the separation column 201 may include an alkali metal salt. In this regard, the second reboiler 202 and the second condenser 203 may be maintained at a temperature of 60 to 110° C. and 0 to 60° C., respectively.

In the second distillation device 200, epichlorohydrin may be additionally generated.

These examples are for illustrative purposes only and are not intended to limit the scope of the present invention.

EXAMPLE

Preparation of Chlorohydrins and Epichlorohydrin from Glycerol and Hydrogen Chloride Gas in the Presence of an Acetic Acid Catalyst By using the manufacturing process illustrated in FIG. 1, glycerol was reacted with hydrogen chloride gas in the presence of an acetic acid catalyst to prepare chlorohydrins and epichlorohydrin. Specifications and operating conditions of devices used in the manufacturing process are shown in Table 1 below:

TABLE 1

| | Specifications of device | Operating conditions | |
|---|---|---|---|
| First reactor | CSTR | 120° C., 4 atm | |
| Two mixing devices | vacuum ejector | — | |
| Two decompression devices | decompression valve | 46 mmHg | |
| Water removal device | vacuum distillation | dehydration column | theoretical plate number: 20, pressure: 23 mmHg |
| | | reboiler | 114° C., 46 mmHg |
| | | condenser | 49° C., 23 mmHg |
| Second reactor | CSTR | 120° C., 4 atm | |
| First distillation device (rear end of water removal device) | vacuum distillation | separation column | theoretical plate number: 20, pressure: 23 mmHg |
| | | reboiler | 127° C., 46 mmHg |
| | | condenser | 56° C., 23 mmHg |
| Stripping device | steam stripping | stripping device | 152 mmHg |
| | | steam | 143° C., 3 atm |
| Inline reactor | tubular reactor | | 70° C., 1 atm |
| Second distillation device (rear end of inline reactor) | vacuum distillation | separation column | theoretical plate number: 20, |
| | | reboiler | 104° C., 1 atm |
| | | condenser | 35° C., 1 atm |

In addition, a total flow rate of materials transported via the respective lines in the manufacturing procedure, constituents of the materials, and flow rates of the respective constituents were respectively measured, and results thereof are shown in Table 2 below. Flow rates of the respective constituents were calculated as follows: the total flow rates of materials transported through the respective lines were measured, component ratios of materials collected from the respective lines were analyzed by a gas chromatograph, and the total flow rates was multiplied by component ratios of the materials.

TABLE 2

| Line number | Total flow rate (Kg/hr) | Components of Materials transported | Flow rate (Kg/hr) |
|---|---|---|---|
| 1 | 315 | glycerol | 300 |
| | | acetic acid | 15 |
| 2 | 228 | HCl | 228 |
| 3 | 5713 | monochloropropanediol | 555 |
| | | dichloropropanol | 3444 |
| | | glycerol acetates | 229 |
| | | water | 1083 |
| | | glycerol | 78 |
| | | HCl | 269 |
| | | acetic acid | 55 |
| 4 | 543 | monochloropropanediol | 53 |
| | | dichloropropanol | 327 |
| | | glycerol acetates | 22 |
| | | water | 103 |
| | | glycerol | 7 |
| | | HCl | 26 |
| | | acetic acid | 5 |
| 5 | 250 | dichloropropanol | 116 |
| | | water | 103 |
| | | HCl | 26 |
| | | acetic acid | 5 |
| 6 | 293 | monochloropropanediol | 53 |
| | | dichloropropanol | 211 |
| | | glycerol acetates | 22 |
| | | glycerol | 7 |
| 7 | 6382 | monochloropropanediol | 268 |
| | | dichloropropanol | 5431 |
| | | glycerol acetates | 443 |
| | | water | 188 |
| | | glycerol | 6 |
| | | HCl | 46 |
| 8 | 21 | HCl | 21 |
| 9 | 314 | monochloropropanediol | 13 |
| | | dichloropropanol | 268 |
| | | glycerol acetates | 22 |
| | | water | 9 |
| | | glycerol | 0 |
| | | HCl | 2 |
| 10 | 254 | dichloropropanol | 243 |
| | | water | 9 |
| | | HCl | 2 |
| 11 | 60 | monochloropropanediol | 13 |
| | | dichloropropanol | 25 |
| | | glycerol acetates | 22 |
| | | glycerol | 0 |
| 12 | 60 | steam | 60 |
| 13 | 85 | monochloropropanediol | 2 |
| | | dichloropropanol | 24 |
| | | water | 59 |
| 14 | 35 | monochloropropanediol | 11 |
| | | dichloropropanol | 1 |
| | | glycerol acetates | 22 |
| | | water | 1 |
| | | glycerol | 0 |
| 15 | 589 | monochloropropanediol | 2 |
| | | dichloropropanol | 383 |
| | | water | 171 |
| | | glycerol | 0 |
| | | HCl | 28 |
| | | acetic acid | 5 |
| 16 | 2000 | water | 2000 |
| 17 | 640 | NaOH | 160 |
| | | water | 480 |
| 18 | 3229 | dichloropropanol | 8 |
| | | epichlorohydrin | 268 |
| | | water | 2718 |
| | | glycerol | 3 |
| | | sodium acetate | 7 |
| | | NaCl | 215 |
| | | NaOH | 10 |
| 19 | 274 | dichloropropanol | 0 |
| | | epichlorohydrin | 272 |
| | | water | 2 |
| 20 | 2955 | water | 2718 |
| | | glycerol | 4 |
| | | sodium acetate | 7 |
| | | NaCl | 219 |
| | | NaOH | 7 |

Evaluation Example

During reaction, samples were collected from the line 4 and the line 15 at an interval of 5 minutes, and then, constituents of the samples and content ratios of the respective constituents were analyzed by a gas chromatograph. Analysis data obtained after reaching a steady state was used to calculate a conversion rate of glycerol, a yield of monochloropropanediol, a yield of dichloropropanol, selectivity of monochloropropanediol, and selectivity of dichloropropanol, according to Equations 1 to 5. Results thereof are shown in Table 3 below.

TABLE 3

|  | Sample collection site | |
| --- | --- | --- |
|  | line 4 | line 15 |
| Glycerol conversion rate (%) | 97.5 | 100 |
| Monochloropropanediol yield (%) | 14.6 | 0.6 |
| Dichloropropanol yield (%) | 77.9 | 94.2 |
| Chlorohydrins yield[*1] (%) | 92.5 | 94.8 |
| Monochloropropanediol selectivity (%) | 14.6 | 0.6 |
| Dichloropropanol selectivity (%) | 77.9 | 94.2 |
| Chlorohydrins selectivity[*2] (%) | 92.5 | 94.8 |

[*1] monochloropropanediol yield + dichloropropanol yield
[*2] monochloropropanediol selectivity + dichloropropanol selectivity Referring to Table 3, the sample collected from line 15 has a very high yield (94.8%) and a very high selectivity (94.8%). In addition, the yield and selectivity of dichloropropanol were much higher than the yield and selectivity of monochloropropanediol.

While the present invention has been particularly shown and described with reference to drawings and exemplary embodiments thereof, it will be understood by those of ordinary skill in the art that various changes in form and details may be made therein without departing from the spirit and scope of the present invention as defined by the following claims.

The invention claimed is:

1. A method of preparing chlorohydrins by reacting polyhydroxy aliphatic hydrocarbon with a chlorination agent in the presence of a catalyst, the method comprising at least one combination of a series of unit operations comprising the following steps in the following stated order:
a first reaction step for reacting polyhydroxy aliphatic hydrocarbon with a chlorination agent;
a water removal step for removing water as a by-product from a reaction mixture discharged from the first reaction step; and
a second reaction step for reacting at least one constituent of the reaction mixture from which water is removed, with at least one of the chlorination agent and an additional chlorination agent,
wherein the reaction mixture introduced into the water removal step comprises polyhydroxy aliphatic hydrocarbon, chlorohydrins, and an intermediate product as a reaction product of the catalyst and the polyhydroxy aliphatic hydrocarbon at a ratio of 0 to 90 parts by weight of the polyhydroxy aliphatic hydrocarbon: 5 to 95 parts by weight of the chlorohydrins: 5 to 12 parts by weight of the intermediate product, and
the water removal step is performed by distillation based on a boiling point difference between constituents of the reaction mixture added to the water removal step, wherein the effluent of the first reactor introduced into the water removal step comprises the chlorination agent and water at a ratio of 10 to 25.0 parts by weight of the total of the chlorination agent and the additional chlorination agent and 75 to 90 parts by weight of water so that the effluent of the first reactor introduced into the water removal step forms an azeotropic mixture.

2. A method of preparing chlorohydrins, the method comprising:
introducing polyhydroxy aliphatic hydrocarbon, a catalyst, and a chlorination agent into a first reactor in which the temperature is maintained in a range of 50 to 200° C.;
discharging an effluent of the first reactor comprising water as a by-product from the first reactor;
introducing at least a portion of the effluent of the first reactor effluent into a water removal device; and
introducing the effluent of the first reactor from which water is removed, and an additional chlorination agent into a second reactor in which the temperature is maintained in a range of 80 to 200° C.,
wherein the effluent of the first reactor introduced into the water removal device comprises polyhydroxy aliphatic hydrocarbon, chlorohydrins, and an intermediate product as a reaction product of the catalyst and the polyhydroxy aliphatic hydrocarbon at a ratio of 0 to 90 parts by weight of the polyhydroxy aliphatic hydrocarbon: 5 to 95 parts by weight of the chlorohydrins: 5 to 12 parts by weight of the intermediate product, and
the water removal device is operated by distillation operation based on a boiling point difference between constituents of the reaction mixture added to the water removal device; wherein the effluent of the first reactor introduced into the water removal step comprises the chlorination agent and water at a ratio of 10 to 25.0 parts by weight of the total of the chlorination agent and the additional chlorination agent and 75 to 90 parts by weight of water so that the effluent of the first reactor introduced into the water removal step forms an azeotropic mixture.

3. The method of claim 1, wherein the polyhydroxy aliphatic hydrocarbon is a $C_2$ to $C_{20}$ compound that has two or more hydroxyl groups bonded to different carbon atoms.

4. The method of claim 3, wherein the polyhydroxy aliphatic hydrocarbon is selected from the group consisting of 1,2-ethanediol, 1,2-propanediol, 1,3-propanediol, 3-chloro-1,2-propanediol, 2-chloro-1,3-propanediol, glycerol, 1,2,4-butanetriol, 1,4-butanediol, esters of these compounds and mixtures thereof.

5. The method of claim 1, wherein the chlorohydrins are a compound having at least one hydroxyl group and at least one chlorine atom that are bonded to different carbon atoms.

6. The method of claim 5, wherein the chlorohydrins comprise at least one compound selected from the group consisting of 3-chloro-1,2-propanediol, 2-chloro-1,3-propanediol, 1,3-dichloropropane-2-ol, and 2,3-dichloropropane-1-ol.

7. The method of claim 1, wherein the catalyst comprises at least one selected from the group consisting of an organic acid catalyst, a carboxylic acid-based catalyst, a nitrile-based catalyst, and a solid catalyst.

8. The method of claim 1, wherein the intermediate product acts as a catalyst in a chlorination reaction of the polyhydroxy aliphatic hydrocarbon.

9. The method of claim 8, wherein the polyhydroxy aliphatic hydrocarbon is glycerol, the catalyst is an acetic acid, and the intermediate product is glycerol acetate.

10. The method of claim 1, wherein the chlorination agent comprises a hydrogen chloride gas or an aqueous hydrochloric acid solution.

11. The method of claim 2, wherein the effluent of the first reactor introduced into the water removal device is discharged when a conversion rate of the polyhydroxy aliphatic hydrocarbon is in a range of 30 to 100% and the yield of the chlorohydrins is in a range of 30 to 95%, in the first reactor.

12. The method of claim 2, wherein a chlorination agent is additionally introduced into the second reactor.

13. The method of claim 2, wherein a retention time of the reactor contents in the first reactor is in a range of 20 minutes to 1 hour, and a retention time of the reactor contents in the second reactor is in a range of 1 to 3 hours.

14. The method of claim 2, wherein the first reactor and the second reactor are maintained at an atmospheric pressure or higher, and the water removal device is maintained at an atmospheric pressure or lower.

15. The method of claim 14, wherein the first reactor and the second reactor are maintained at 1 to 20 atm, and the water removal device is maintained at 10 to 760 mmHg.

16. The method of claim 15, wherein the water removal device comprises a vacuum distillation column having a theoretical plate number of 2 to 50.

17. The method of claim 14, wherein the effluent of the first reactor is decompressed in a decompression device and then introduced into the water removal device.

18. The method of claim 17, wherein the decompression device comprises a decompression valve.

19. The method of claim 2, wherein the first reactor and the second reactor are each independently a continuous stirred tank reactor, a batch reactor, a semi-batch reactor, or a plug flow reactor.

20. The method of claim 2, wherein the effluent of the first reactor introduced into the water removal device is divided into a water-rich layer and a water-deficient layer.

21. The method of claim 20, further comprising: purifying chlorohydrins from an effluent of the second reactor to obtain chlorohydrins concentrate, and mixing the water-rich layer with the chlorohydrins concentrate to obtain a first composition of chlorohydrins.

22. The method of claim 21, wherein the effluent of the second reactor comprises 0 to 10 parts by weight of the polyhydroxy aliphatic hydrocarbon, 80 to 98 parts by weight of the chlorohydrins, 0 to 10 parts by weight of the total of the chlorination agent and the additional chlorination agent and 1 to 20 parts by weight of water.

23. The method of claim 22, wherein the first composition of chlorohydrins comprises 0 to 10 parts by weight of the polyhydroxy aliphatic hydrocarbon, 60 to 96 parts by weight of the chlorohydrins, 0 to 20 parts by weight of the total of the chlorination agent and the additional chlorination agent, and 0 to 30 parts by weight of water.

24. The method of claim 21, further comprising diluting the first composition of chlorohydrins with water to obtain the second composition of chlorohydrins.

25. The method of claim 24, wherein the water is added in an amount of 100 to 500 parts by weight based on 100 parts by weight of the first composition of chlorohydrins.

26. The method of claim 2, wherein the polyhydroxy aliphatic hydrocarbon is a $C_2$ to $C_{20}$ compound that has two or more hydroxyl groups bonded to different carbon atoms.

27. The method of claim 26, wherein the polyhydroxy aliphatic hydrocarbon is selected from the group consisting of 1,2-ethanediol, 1,2-propanediol, 1,3-propanediol, 3-chloro-1,2-propanediol, 2-chloro-1,3-propanediol, glycerol, 1,2,4-butanetriol, 1,4-butanediol, esters of these compounds and mixtures thereof.

28. The method of claim 2, wherein the chlorohydrins are a compound having at least one hydroxyl group and at least one chlorine atom that are bonded to different carbon atoms.

29. The method of claim 28, wherein the chlorohydrins comprise at least one compound selected from the group consisting of 3-chloro-1,2-propanediol, 2-chloro-1,3-propanediol, 1,3-dichloropropane-2-ol, and 2,3-dichloropropane-1-ol.

30. The method of claim 2, wherein the catalyst comprises at least one selected from the group consisting of an organic acid catalyst, a carboxylic acid-based catalyst, a nitrile-based catalyst, and a solid catalyst.

31. The method of claim 2, wherein the intermediate product acts as a catalyst in a chlorination reaction of the polyhydroxy aliphatic hydrocarbon.

32. The method of claim 31, wherein the polyhydroxy aliphatic hydrocarbon is glycerol, the catalyst is an acetic acid, and the intermediate product is glycerol.

33. The method of claim 2, wherein the chlorination agent comprises a hydrogen chloride gas or an aqueous hydrochloric acid solution.

* * * * *